United States Patent
Tummala et al.

(10) Patent No.: US 10,383,943 B2
(45) Date of Patent: Aug. 20, 2019

(54) COMPOSITIONS AND RELATED METHODS FOR THE TREATMENT OF CANCER

(71) Applicant: South Dakota Board of Regents, Pierre, SD (US)

(72) Inventors: Hemachand Tummala, Brookings, SD (US); Pratik Muley, Brookings, SD (US)

(73) Assignee: South Dakota Board of Regents, Pierre, SD (US)

( * ) Notice: Subject to any disclaimer, the term of this patent is extended or adjusted under 35 U.S.C. 154(b) by 0 days.

(21) Appl. No.: 15/441,191

(22) Filed: Feb. 23, 2017

(65) Prior Publication Data

US 2017/0239361 A1 Aug. 24, 2017

Related U.S. Application Data

(60) Provisional application No. 62/298,731, filed on Feb. 23, 2016.

(51) Int. Cl.
*A61K 45/06* (2006.01)
*A61K 31/555* (2006.01)
*A61K 47/54* (2017.01)

(52) U.S. Cl.
CPC ............ *A61K 45/06* (2013.01); *A61K 31/555* (2013.01); *A61K 47/542* (2017.08); *A61K 47/549* (2017.08)

(58) Field of Classification Search
None
See application file for complete search history.

(56) References Cited

PUBLICATIONS

Ahmad, Z. et al. Macromol Biosci 2014 vol. 14, pp. 1337-1345.*
Desale, S. et al., J. Controlled Release 2015 vol. 220 pp. 651-659.*
Mukhopadhyay, S. et al., Bioconj. Chem. 2008 vol. 19, pp. 39-49.*
Wang, X. et al., Chem. Soc. Rev. 2013 vol. 42, pp. 202-224.*
Annibaldi et al., "Glucose metabolism in cancer cells", "Current Opinion in Clinical Nutrition and Metabolic Care", 2010, pp. 466-470, vol. 13.
Becker et al., "Immune-suppresive properties of the tumor microenvironment", "Cancer Immunol Immunother", 2013, pp. 1137-1148, vol. 62.
Boyle et al., "Breast Cancer Stem Cells and the Immune System: Promotion, Evasion and Therapy", "J Mammary Glad Biol Neoplasia", 2014, pp. 203-211, vol. 19.
Corthay, A., "Does the Immune System Naturally Protect Against Cancer?", "Frontiers in Immunology", 2014, p. 197, vol. 5.
Doherty et al., "Targeting lactate metabolism for cancer therapeutics", "The Journal of Clinical Investigation", 2013, pp. 3685-3692, vol. 123, No. 9.
Gajewski et al., "Innate and adaptive immune cells in the tumor microenvironment", "Nat Immunol", 2013, pp. 1014-1022, vol. 14, No. 10.
Ganapathy et al., "Nutrient transporters in cancer: Relevance to Warburg hypothesis and beyond", "Pharmacology and Therapeutics", 2009, pp. 29-40, vol. 121.
Gough et al., "Immune system plays an important role in the success and failure of conventional cancer therapy", "Immunotherapy", 2012, pp. 125-128, vol. 4, No. 2.
Husain et al., "Tumor-derived lactate modifies antitumor immune response: effect on myeloid-derived suppressor cells and NK cells", "The Journal of Immunology", 2013, pp. 1486-1495, vol. 191.
Kaur et al., "Radiation-induced effects and the immune system in cancer", "Frontiers in Oncology", 2012, p. 191 vol. 2.
Lee et al., "Immune Responses and the Tumor Microenvironment: How They Communicate to Regulate Gastric Cancer", "Gut and Liver", 2014, pp. 131-139, vol. 8, No. 2.
Narendra et al., "Immune system: a double-edged sword in cancer", "Inflamm. REs.", 2013, pp. 823-834, vol. 62, No. 9.
Semenza, G. L., "Tumor metabolism: cancer cells give and take lactate", "the Journal of Clinical Investigation", 2008, pp. 3835-3837, vol. 118, No. 12.
Nang et al., "L-type amino acid transport and cancer: targeting the mTORC1 pathway to inhibit neoplasia", "Am J Cancer Res", 2015, pp. 1281-1294, vol. 5, No. 4.
Desoize et al., "Particular Aspects of Platinum Compounds Used at Present in Cancer Treatment", "Oncology Hematology", 2002, pp. 317-325, vol. 42.
Ding et al., "Conjugated polyelectrolyte-cisplatin complex nanoparticles for simultaneous in vivo imaging and drug tracking", "Nanoscale", 2011, pp. 1997-2002, vol. 3.
Florea et al., "Cisplatin as an Anti-Tumor Drug: Cellular Mechanisms of Activity, Drug Resistance and Induced Side Effects", "Cancers", 2011, pp. 1351-1371, vol. 3.
Florea et al., "Occurence, use and potential toxic effects of metals and metal compounds", "Biometals", 2006, pp. 419-427, vol. 19.
Huo et al., "Preparation, Biodistribution and Neurotoxicity of Liposomal Cisplatin following Convection Enhanced Delivery in Normal and F98 Glioma Bearing Rats", "PLOS One", 2012, pp. 2895-2900, vol. 7, No. 11.
Peng et al., "Targeted Delivery of Cisplatin to Lung Cancer Using ScFvEGFR-Heparin-Cisplatin Nanoparticles", "ACS Nano", 2011, pp. 9480-9493, vol. 5, No. 12.
Shah et al., "New-generation platinum agents for solid tumors", "Future Oncology", 2009, pp. 33-42, vol. 5.

(Continued)

*Primary Examiner* — Heidi Reese
(74) *Attorney, Agent, or Firm* — Davis, Brown, Koehn, Shors & Roberts, P.C.; Matthew W. Coryell; Sean D. Solberg

(57) ABSTRACT

Compositions and methods for the use thereof for the treatment of cancer in a subject in need thereof comprising administering to the subject an effective amount of a composition comprising an anticancer composition comprising a antineoplastic compound and a conjugated targeting moiety with or without a chemical linker. In certain aspects the antineoplastic compound is a platin and the conjugated targeting moiety is an amino acid.

16 Claims, 12 Drawing Sheets

(56) References Cited

PUBLICATIONS

Spanos et al., "Immune Response During Therapy With Cisplatin or Radiation for Human Papillomavirus-Related Head and Neck Cancer", "Arch Otolaryngol Head Neck Surg.", 2009, pp. 1137-1146, vol. 135, No. 11.

Xiao et al., "Biodegradable polymer—cisplatin (IV) conjugate as a pro-drug of cisplatin (II)", "Biomaterials", 2011, pp. 7732-7739, vol. 32, No. 30.

Yallapu et al., "Curcumin nanoformulations: a future nanomedicine for cancer", "Drug Discovery Today", 2011, pp. 71-80, vol. 17, No. 12.

Zhao, "Tumor Microenvironment in Pathogenesis and Drug Resistance of Non-Hodgkin's Lymphoma", "Zhonghua Xue Ye Xue Za Zhi", 2014, pp. 466-469, vol. 35, No. 5.

* cited by examiner

NMR Analysis

Mass spectra of Cisplatin 4AP conjugate after purification.

AT-Platin

A.

AT$_2$-Platin

B.

Cisplatin

A-Platin – binds to LAT1

Cisplatin-Tyrosine
　　No free $NH_2$ or COOH group to bind to LAT1

IC50 of Cisplatin 4AP: 38.265uM

IC50 of Cisplatin 4AP: 85.265uM 6 hour treatment followed by 72 hour incubation in Ovcar3 (Ovarian Cancer cells) and IOSE cells (non-cancer, ovarian epithelial cells)

A-Platin does not reduce the WBC counts in mice as much as cisplatin.
WBC counts are important for strong immune clearance of tumor.

A-Platin

With -Boc protecting group

◯ = amino acid (phenyl alanine)

G-Platin

○ = Glucose

AT2-platin is similar to AT-platin but two amino acids are attached instead of one

COMPOSITIONS AND RELATED METHODS FOR THE TREATMENT OF CANCER

CROSS-REFERENCE TO RELATED APPLICATION(S)

This Application claims the benefit of U.S. Provisional Application No. 62/298,731, filed on Feb. 23, 2016; which is incorporated herein by reference in its entirety.

FIELD OF THE INVENTION

Disclosed herein are methods and compositions for treating cancer.

BACKGROUND OF THE INVENTION

Cancer is the second leading cause of deaths in the USA, accounting for nearly one of every four deaths. It is estimated that in the USA there will be more than 1.6 million new cases of cancers with more than 535,000 deaths associated with cancer in 2014 alone. Existing treatments are limited by server side effects owing to non-specific drug actions on non-cancer cells. A recent concept in cancer therapy is that strong immune surveillance is capable of detecting and eliminating cancer cells. Research has shown that an active immune system is needed to clear tumors after chemotherapy with a commonly used anti-cancer drug, cisplatin. Ironically, cisplatin adversely affects the patient's immune system by killing white blood cells (WBC) and, importantly, solid tumors usually escape immune destruction by suppressing the anti-cancer immunity at the tumor site by creating a unique micro-environment through metabolic alterations. Furthermore, cisplatin treatment has the significant drawback of dose dependent side effects. The side effects of cisplatin chemotherapy include general cell damaging effects such as nausea and vomiting, bone marrow suppression and immunesuppression. More specifically, cisplatin causes acute kidney damage (nephrotoxicity) and hearing loss (ottotoxicity).

Many approaches have been tried to reduce cisplatin toxicity. Drug delivery approaches such as formulation of cisplatin containing liposomes, nanoparticles and complexes did not result in significant advantage and failed to receive any substantial clinical attention. Chemical modification approaches such as derivatising cisplatin and conjugating cisplatin to polymers have also been tried with limited success. These are complex procedures that may not suitable for clinical application. Accordingly, there is a need in the art to target cisplatin and other chemotherapeutic drugs to tumor cells to maximize efficacy while minimizing side effects.

BRIEF SUMMARY OF THE INVENTION

Disclosed herein, is an anticancer composition comprising a antineoplastic compound and a conjugated targeting moiety with or without a chemical linker. In certain aspects, the antineoplastic compound is a platin. According to further aspects, the platin is cisplatin. In certain further aspects, the antineoplastic compound is taxol family, including but not limited to paclitaxel, and Docetaxel, nucleotide analogs such as a gemcitabine and 5-fluorouracil and doxorubicin. In yet further aspects, the conjugated targeting moiety is an amino acid, a saccharide, a metal ion or a fatty acid. In still further aspects, the conjugated targeting moiety is an amino acid. According to still further aspects, the amino acid is selected from a group comprising: leucine, isoleucine, histidine, methionine, phenylalanine, tyrosine, valine, and tryptophan. In further aspects, the amino acid is phenylalanine.

According to certain aspects, the conjugated targeting moiety binds L-type amino acid transporter (LAT) or ASCT. In certain aspects, the composition has greater cancer cell killing efficacy than the antineoplastic compound without the conjugated targeting moiety. In still further aspects, the instantly disclosed composition has greater potency than the antineoplastic compound without the conjugated targeting moiety. In yet further aspects, administration of the composition induces less toxicity than administration of the antineoplastic compound without the conjugated targeting moiety. According to still further aspects, administration of the composition induces less nephrotoxicity or immune toxicity than administration of the antineoplastic compound without the conjugated targeting moiety.

Disclosed herein, is anticancer composition, having the structure:

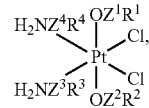

wherein R1 is selected from hydrogen, an amino acid, a saccharide, a metal ion or a fatty acid and wherein Z1 is an optionally present linker and wherein when R1 is a hydrogen, Z1 is absent; wherein R2 is selected from hydrogen, an amino acid, a saccharide, a metal ion or a fatty acid and wherein Z2 is an optionally present linker and wherein when R2 is a hydrogen, Z2 is absent; wherein R3 is selected from hydrogen, an amino acid, a saccharide, a metal ion or a fatty acid and wherein Z3 is an optionally present linker and wherein when R3 is a hydrogen, Z3 is absent; wherein R4 is selected from hydrogen, an amino acid, a saccharide, a metal ion or a fatty acid and wherein Z4 is an optionally present linker and wherein when R4 is a hydrogen, Z4 is absent.

Disclosed herein is an anticancer composition, having the structure:

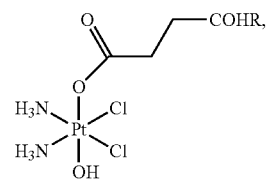

wherein R is an amino acid, a metal ion, a saccharide, or a fatty acid. According to certain aspects, R is an amino acid and the amino acid is phenylalanine.

Disclosed herein is an anticancer composition comprising a compound having the structure:

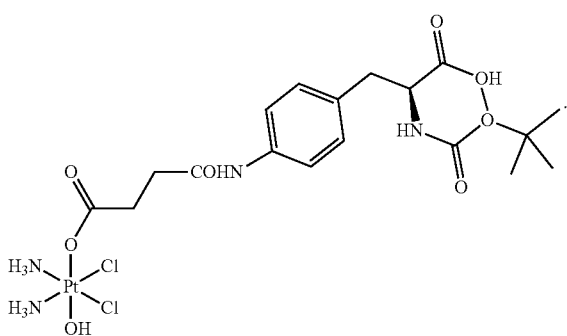

Disclosed herein is an anticancer composition comprising a compound having the structure:

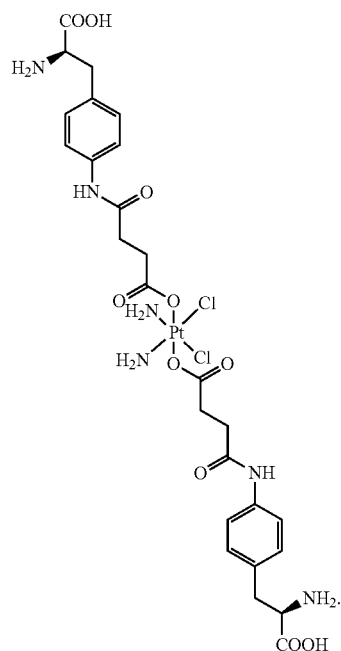

Disclosed herein is an anticancer composition comprising a compound having the structure:

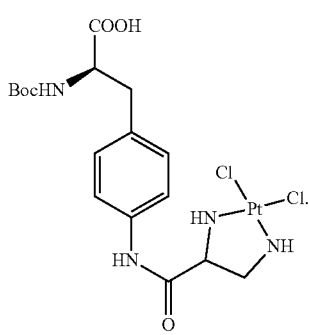

Disclosed herein is a method for treating cancer in a subject in need thereof, the method comprising administering to the subject an effective amount of the composition disclosed herein and a pharmaceutically acceptable carrier thereof. In certain aspects, the composition is administered in a therapeutically effective amount. According to further aspects, the composition induces tumor cell clearance. According to still further aspects, the method further comprises administering the composition intravenously, intraperitoneally, intramuscularly, orally, subcutaneously, intraocularly, intra-tumor injection or transdermally or delivered directly to tumor organ by invasive techniques. According to still further aspects, the disclosed method further comprises administering the composition in conjunction with at least one other treatment or therapy. In certain aspects, the other treatment or therapy comprises co-administering another anti-neoplastic agent. In still further aspects, the compound is administered alone or in combination with other chemical based therapeutics, radiation therapy, thermal therapy, physical therapy, phototherapy, or dietary therapy. In even further aspects, the administration is for prophylactic or therapeutic purposes.

DETAILED DESCRIPTION

Figure 1:
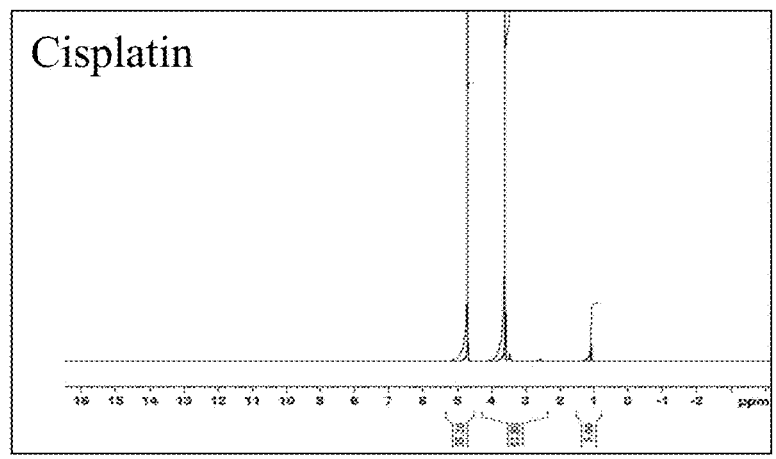
FIG. 1 shows data from NMR analysis of cisplatin and A-platin, according to certain embodiments.
Figure 1:
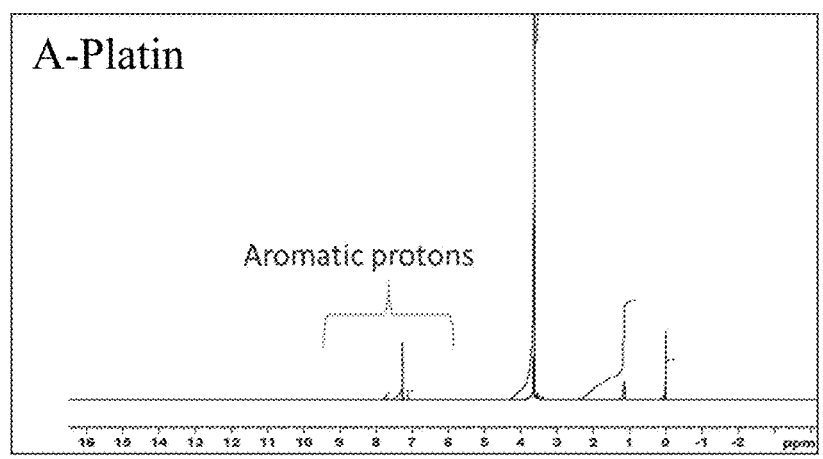

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH2CH2O— units in the polyester, regardless of whether ethylene glycol was used to prepare the polyester. Similarly, a sebacic acid residue in a polyester refers to one or more —CO(CH2)8CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A1," "A2," "A3," and "A4" are used herein as generic symbols to represent various specific substituents. These symbols can be any substituent, not limited to those disclosed herein, and when they are defined to be certain substituents in one instance, they can, in another instance, be defined as some other substituents.

"R1," "R2," "R3," "Rn," where n is an integer, as used herein can, independently, possess one or more of the groups listed above. For example, if R1 is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, "cisplatin," means the compound having the structure:

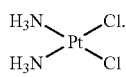

Cisplatin has also been referred to as cisplatinum, platamin, neoplatin, and cismaplator cis-diamminedichloroplatinum (II) (CDDP).

As used herein, A-platin, also referred to herein as cisplatin-4AP, means the Cisplatin (IV) Phenylalanine Prodrug with Boc protecting group having the structure:

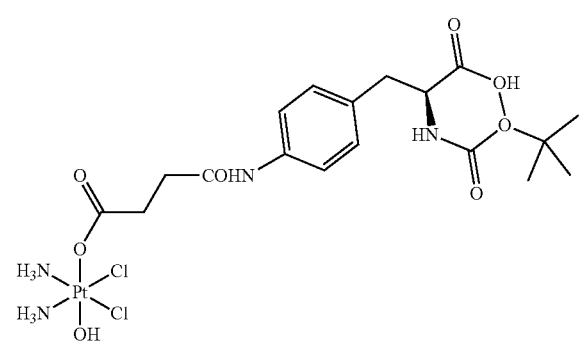

As used herein, AT-platin, means the Cisplatin (IV) Phenylalanine Prodrug without Boc protecting group, having the structure:

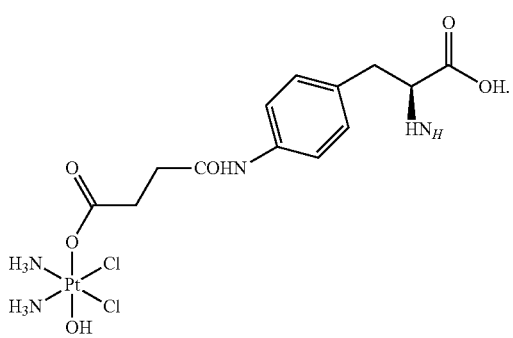

As used herein, AT2-platin means the Cisplatin phenylalanine prodrug having the formula:

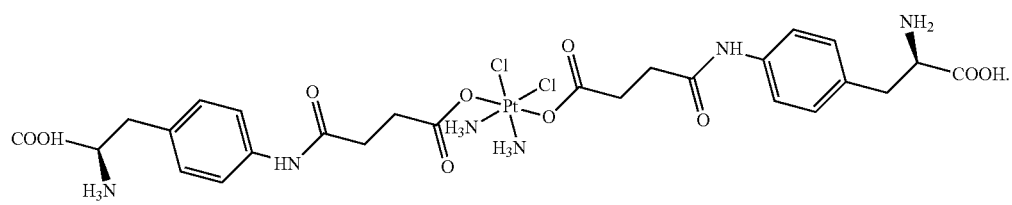

As used herein, G-platin means a cisplatin prodrug composition, having the formula:

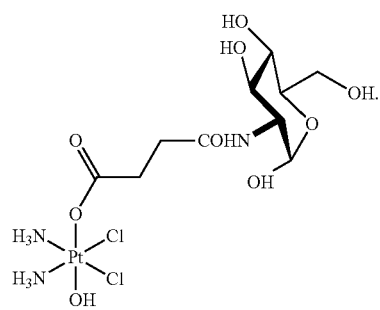

As used herein, "targeting moiety" means a moiety capable of binding nutritional transporters overexpressed in cancer cells or any other tissue. Examples include but are not limited to amino acids (e.g. phenylalanine), metal ions (e.g. Zn), saccharides (e.g. glucose) and fatty acids (e.g. palmitate). Nutritional transporters known to be overexpressed in cancer cells include, but are not limited to, LAT1 (L-type amino acid transporter 1), LAT (Large Neutral Amino Acid Transporter), ASCT, xCT, CAT, GLUT (Glucose Transporter) and OATP (Organic Anion Transporting Polypeptide).

As used herein, the term "pharmaceutically acceptable carrier" or "carrier" refers to sterile aqueous or nonaqueous solutions, colloids, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. In some embodiments, the present methods can be used to treat a subject having an epithelial cancer, e.g., a solid tumor of epithelial origin, e.g., lung, breast, ovarian, prostate, renal, pancreatic, or colon cancer.

As used herein, the term "subject" refers to the target of administration, e.g., an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more cancer disorders prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can reduce tumor size or slow rate of tumor growth. A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, administration to specific organs through invasion, intramuscular administration, intratumoral administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The phrase "anti-cancer composition" can include compositions that exert antineoplastic, chemotherapeutic, antiviral, antimitotic, antitumorgenic, anti-angiogenic, anti-metastatic and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/ protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Disclosed is an anticancer composition comprising a antineoplastic compound and a conjugated targeting moiety. According to certain aspects, the antineoplastic compound is a platin. As used herein "platin" means any platinum based compound with known anti-cancer properties. In further aspects, the platin is a cisplatin. In still further aspects, the conjugated targeting moiety is an amino acid, a saccharide, or a fatty acid. In still further aspects, the conjugated targeting moiety is an amino acid. According to certain embodiments the amino acid is selected from a group consisting of histidine, isoleucine, leucine, lysine, methionine, phenylalanine, threonine, tryptophan, valine, alanine, arginine, asparagin, aspartic aci, cysteine, glutamic acid, glutamine, glycine, proline, selenocysteine, serine, and tyrosine. In further embodiments, the amino acid is selected from a group consisting of leucine, phenylalanine, tyrosine, and tryptophan. In certain embodiments, the amino acid is phenylalanine.

According to certain embodiments, the anti-neoplastic compound is selected from drugs in the Taxol family (e.g. Paclitaxel and Docetaxel). In further embodiments, the anti-neoplastic compound is a nucleotide analog (e.g. gemcitabine, 5-fluorouracil, and doxorubicin).

In certain embodiments, the targeting moiety is conjugated to the antineoplastic compound by way of a linker. In certain aspects, the linker is a covalent bond between the antineoplastic compound and the targeting moiety. In further aspects, the linker is an ionic bond.

According to certain embodiments wherein the antineoplastic compound is cisplatin, the targeting moiety may be conjugated to platinum atom, or either two nitrogen or oxygen atoms. In certain embodiments, multiple targeting moieties are conjugated to antineoplastic compound.

According to certain embodiments, the conjugated targeting moiety binds L-type amino acid transporter 1 (LAT1). In further embodiments, the conjugated targeting moiety binds one or more of any amino acid transporter known in the art.

In certain aspects, the disclosed composition has greater cancer cell killing efficacy than the antineoplastic compound without the conjugated targeting moiety.

In certain aspects, disclosed is an anticancer composition, having the structure:

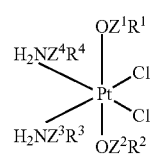

wherein R¹ is selected from hydrogen, an amino acid, a saccharide, a metal ion or a fatty acid and wherein $Z^1$ is an optionally present linker and wherein when $R^1$ is a hydrogen, $Z^1$ is absent; wherein $R^2$ is selected from hydrogen, an amino acid, a saccharide, a metal ion or a fatty acid and wherein $Z^2$ is an optionally present linker and wherein when $R^2$ is a hydrogen, $Z^2$ is absent; wherein $R^3$ is selected from hydrogen, an amino acid, a saccharide, a metal ion or a fatty acid and wherein $Z^3$ is an optionally present linker and wherein when $R^3$ is a hydrogen, $Z^3$ is absent; wherein $R^4$ is selected from hydrogen, an amino acid, a saccharide, a metal ion or a fatty acid and wherein $Z^4$ is an optionally present linker and wherein when $R^4$ is a hydrogen, $Z^4$ is absent.

In certain aspects, disclosed is an anticancer composition, having the structure:

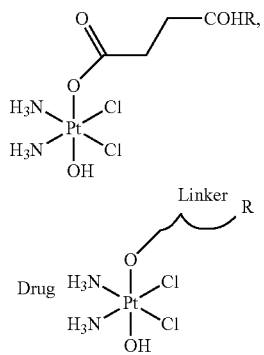

wherein R is an amino acid, a saccharide, a metal ion or a fatty acid.

In certain embodiments, the amino acid phenylalanine.

In certain aspects, disclosed is an anticancer composition comprising a compound having the structure:

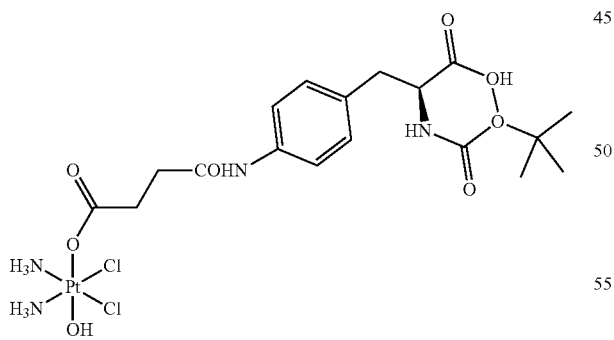

In certain aspects, the disclosed composition further comprises a pharmaceutically suitable carrier thereof.

Figure 3:
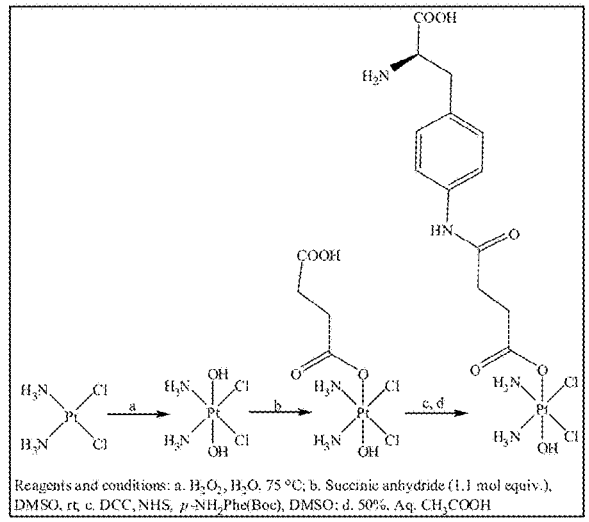
FIG. 3 shows synthesis schemes for AT-platin and $AT_2$-platin, according to certain embodiments.
Figure 3:
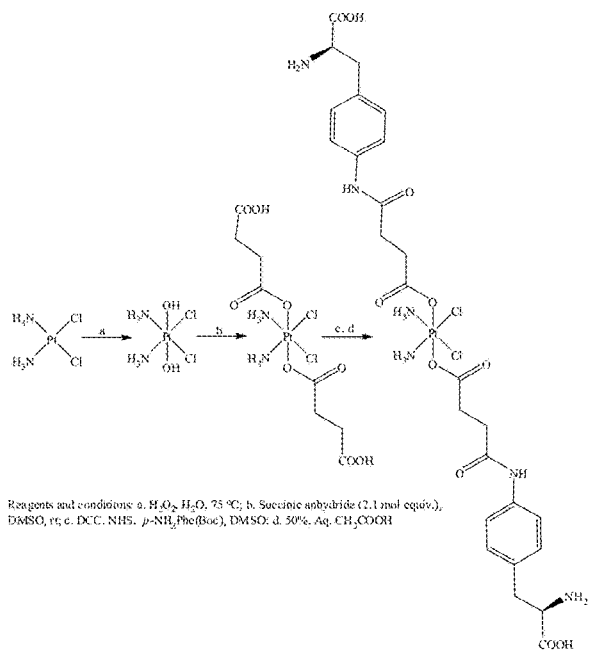

The disclosed composition can be synthesized according to a variety of methods known to those skilled in the art. An exemplary synthesis method is shown in the scheme of FIG. 3 (panel A).

In certain aspects, disclosed is an anticancer composition comprising a compound having the structure:

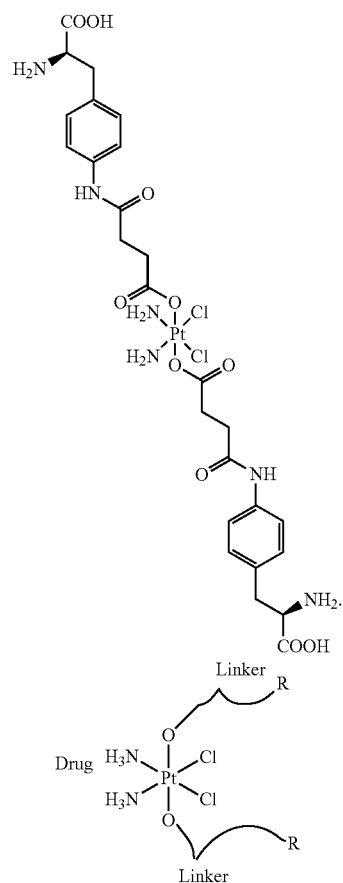

wherein R is an amino acid, a saccharide, metal ion or a fatty acid.

In certain aspects, the disclosed composition further comprises a pharmaceutically suitable carrier thereof.

The disclosed composition can be synthesized according to a variety of methods known to those skilled in the art. An exemplary synthesis method is shown in the scheme of FIG. 3 (panel B).

In certain aspects, disclosed is an anticancer composition comprising a compound having the structure:

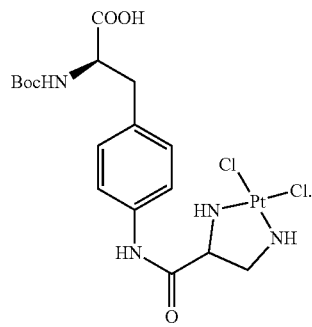

In certain aspects, the disclosed composition further comprises a pharmaceutically suitable carrier thereof.

Figure 4:
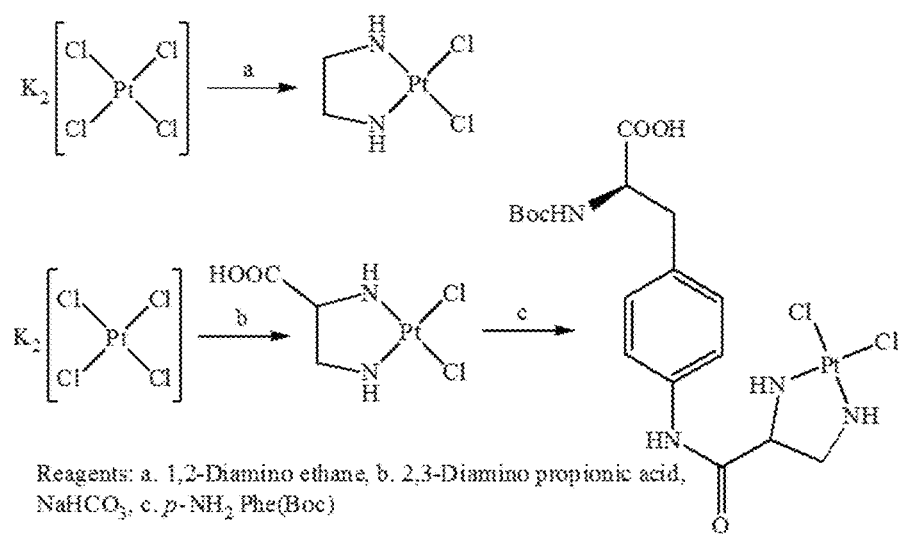
FIG. 4 shows a synthesis scheme of cyclo-platin according to certain embodiments.
Figure 5:
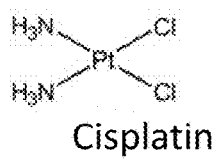
FIG. 5 shows chemical structures cisplatin, A-platin, and cisplatin-tyrosine, according to certain embodiments.
Figure 5:
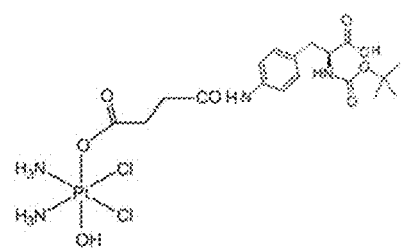
Figure 5:
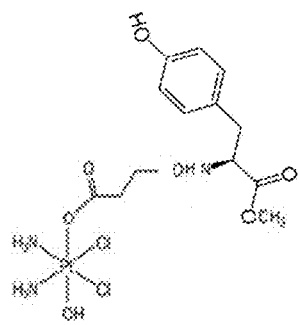

The disclosed composition can be synthesized according to a variety of methods known to those skilled in the art. An exemplary synthesis method is shown in the scheme of FIG. 4.

Also disclosed herein is a method for treating cancer in a subject in need thereof, comprising administering to the subject an effective amount of an anticancer composition disclosed herein and pharmaceutically acceptable carrier thereof.

In certain aspects, the composition is administered in a therapeutically effective amount.

In further aspects, administration of the composition induces tumor cell death.

In yet further aspects, the method further comprises administering the composition intravenously, intraperitoneally, intramuscularly, orally, subcutaneously intraocularly, intra-tumor injection or transdermally or delivered directly to tumor organ by invasive techniques.

According to certain embodiments, administration of the compositions disclosed herein is associated with reduced toxicity compared to administration of a similar of the anti-neoplastic agent not conjugated to the targeting moiety. According to certain further embodiments, administration of the composition induces less toxicity than administration of the antineoplastic compound without the conjugated targeting moiety. In certain implementations, administration of the composition induces less nephrotoxicity than administration of the antineoplastic compound without the conjugated targeting moiety. Without wishing to bound to any particular theory, in these implementations, uptake of composition in the kidney is reduced relative to uptake of the antineoplastic agent without the conjugated targeting moiety.

In still further aspects, the method further comprises administering the composition in conjunction with at least one other treatment or therapy. In even further aspects, the other treatment or therapy comprises co-administering an anti-neoplastic agent. In further aspects, the other treatment or therapy is chemotherapy. In certain aspects, the compound is administered alone or in combination with other chemical based therapeutics or with radiation therapy or thermal therapy or physical therapy or dietary therapy.

In still further aspects, the other therapy is a low carbohydrate ketogenic diet.

According to certain aspects, the subject has been diagnosed with melanoma, breast cancer, lung carcinoma, pancreatic carcinoma, renal carcinoma, ovarian, prostate or cervical carcinoma, glioblastoma, or colorectal carcinoma, cerebrospinal tumor, head and neck cancer, thymoma, mesothelioma, esophageal cancer, stomach cancer, liver cancer, pancreatic cancer, bile duct cancer, bladder cancer, testicular cancer, germ cell tumor, ovarian cancer, uterine cervical cancer, endometrial cancer, lymphoma, acute leukemia, chronic leukemia, multiple myeloma, sarcoma, or any combination thereof.

In certain aspects, the method further comprises administering the composition as a bolus and/or at regular intervals. In certain aspects, the disclosed method further comprises administering the composition intravenously, intraperitoneally, intramuscularly, orally, subcutaneously, intra-tumorally or transdermally.

According to certain further embodiments, the method further comprises diagnosing the subject with cancer. In further aspects, the subject is diagnosed with cancer prior to administration of the composition. According to still further aspects, the method further comprises evaluating the efficacy of the composition. In yet further aspects, evaluating the efficacy of the composition comprises measuring tumor size prior to administering the composition and measuring tumor size after administering the composition. In even further aspects, evaluating the efficacy of the composition occurs at regular intervals. According to certain aspects, the disclosed method further comprises optionally adjusting at least one aspect of method. In yet further aspects, adjusting at least one aspect of method comprises changing the dose of the composition, the frequency of administration of the composition, or the route of administration of the composition.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Figure 2:
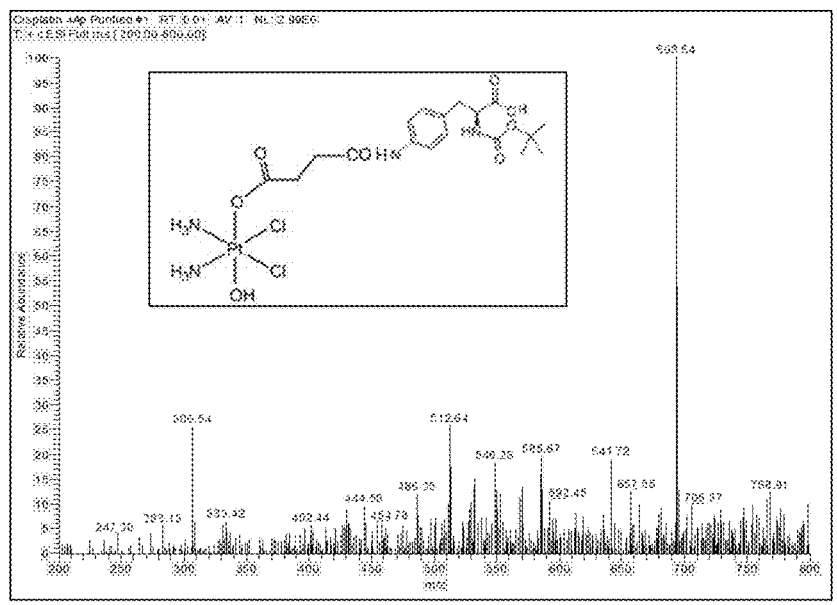
FIG. 2 shows mass spectrometry data of cisplatin 4AP conjugate after purification, according to certain embodiments.

In certain embodiments, A-platin is synthesized and purified according to the following (also shown schematically in FIG. 3). Oxoplatin is synthesized from cisplatin by incubating with hydrogen peroxide for 8 hrs. and purified by precipitating with ice-cold acetone (Yield≅75%). 2) Cisplatin-monosuccinate is synthesized by reacting oxoplatin with succinic anhydride in DMSO and precipitated with ice-cold acetone (yield≅80%). 3) Subsequently, Cisplatin succinate, and triethylamine is incubated in DMSO for 20 min, and then, N,N'-Dicyclohexylcarbodiimide (DCC) will be added and stirred for 1 hr. To this reaction mixture, Boc-4-Amino-L-phenylalanine is added and stirred overnight. The solid is precipitated and washed three times with ice cold acetone. 4) The Boc group is removed from AT-Platin-Boc by reacting with 10% trifluroacetic acid (TFA) in methanol. 5) AT-Platin is further purified by Flash-chromatography with Hexane-Ethyl acetate gradient. The foregoing method consistently yields AT-Platin up to 96% purity. NMR analysis of cisplatin and AT-platin are shown in FIG. 1. A mass spectrometric analysis of AT-platin is shown in FIG. 2.

Figure 6:
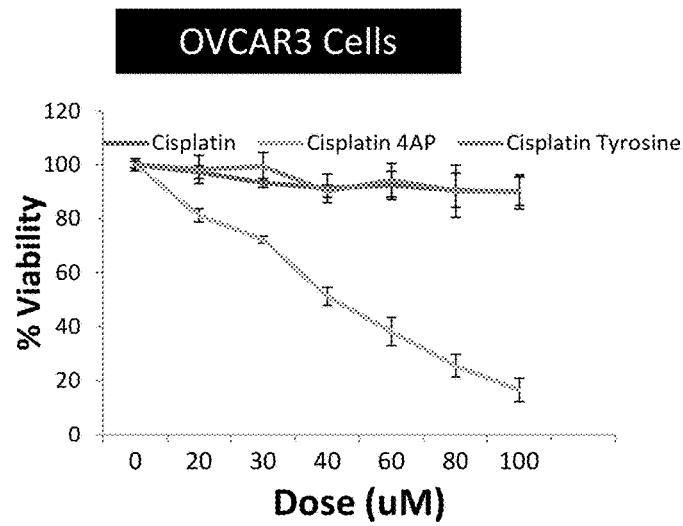
FIG. 6 shows data from cell growth assays, according to certain embodiments.
Figure 6:
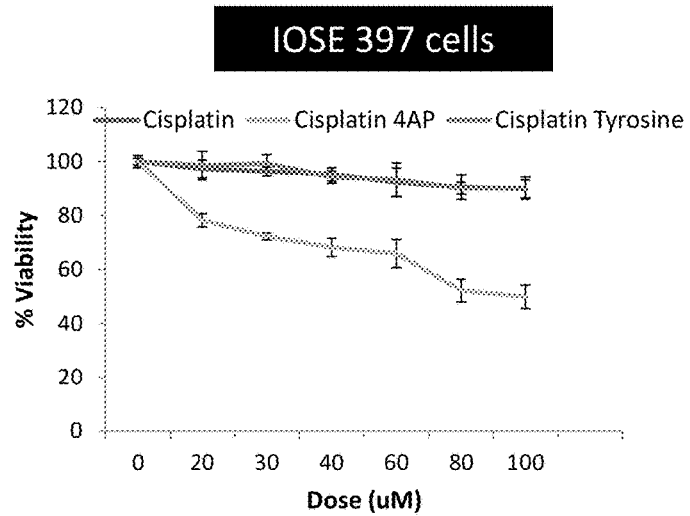

In order to measure the effect of A-platin on cancer cell growth, cell growth assays were performed. 6 hour treatment with cisplatin, cisplatin 4AP, or cisplatin tyrosine was followed by 72 hour incubation in Ovcar3 (Ovarian Cancer cells) and IOSE cells (non-cancer, ovarian epithelial cells). Cell viability was assessed and is shown in FIG. 6. A-platin showed the greatest efficacy in killing cancer cells. Cisplatin tyrosine, which is not expected to bind LAT1 receptors because of a lack of free $NH_2$ or COOH groups, showed a comparable efficacy to cisplatin indicating that the increased efficacy of A-platin is LAT1-recptor dependent.

In order to further assess the effect of A-platin on cancer cell growth, colony forming assays using Head and Neck Squamous Cell Carcinoma (HNSCC) were preformed. Briefly, 10,000 cells were plated in triplicate in 6-well plates per treatment condition. The next day cells were treated with the cisplatin, A-platin, or G-platin at the variable doses. On day 6 from plating, cells were fixed in 70% ethanol and stained with 0.5% crystal violet in 10% ethanol. After sufficient washing and drying, cells were destained in 25% glacial acetic acid, and absorbance of 100 uL of each destain solution was read on a SpectraMax plate reader at 540 nm (A540). A540 is an indirect measure of the amount of crystal violet per well, and thus the number of cells per well.

Figure 7:
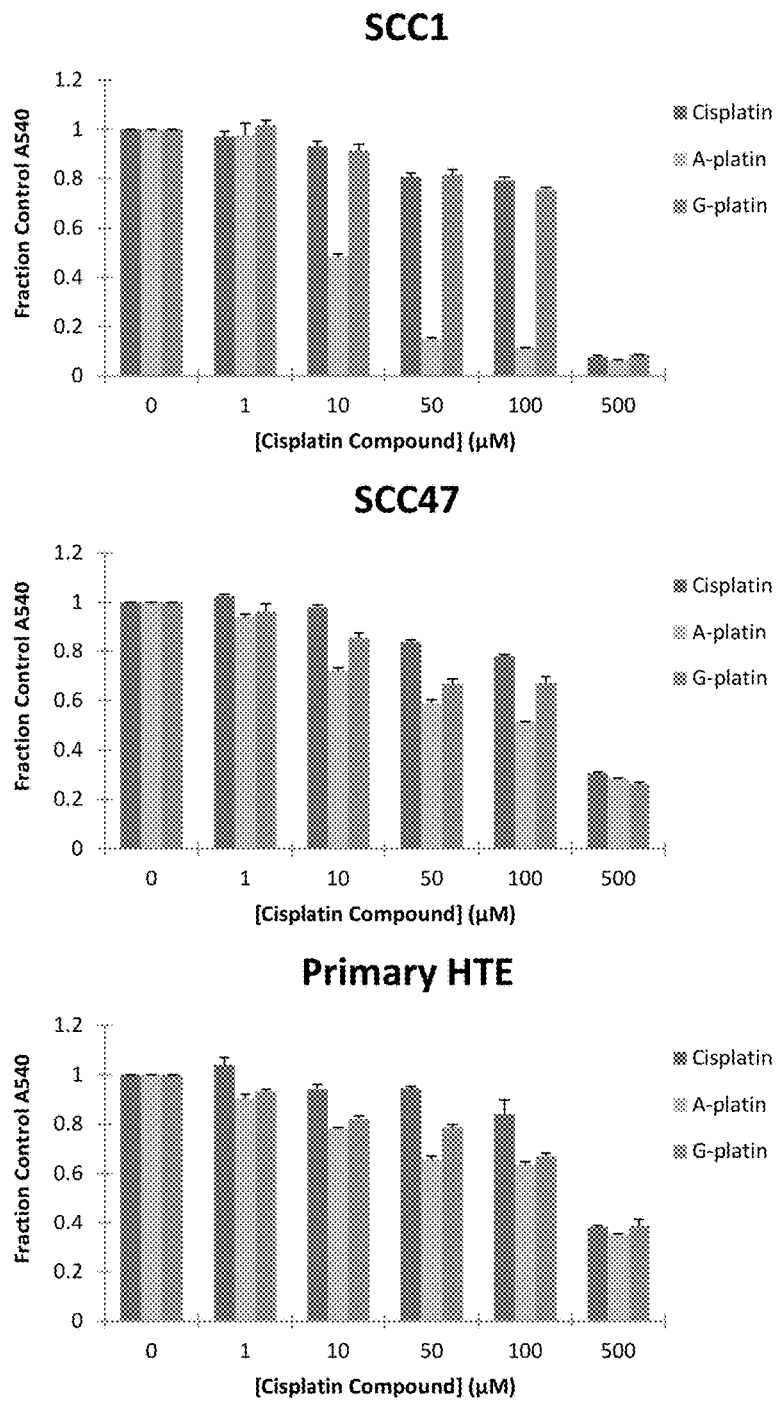
FIG. 7 shows data colony formation assays, according to certain embodiments.

Results are shown in FIG. 7. In SCC1 cells (HPV-human HNSCC), all drugs reduced cell number relative to control (Cisplatin 10-500 µM p<0.03 compared to control, A-platin 10-500 µM p<0.0002 compared to control, and G-platin 10-500 µM p<0.03 compared to control. The data show A-platin to have the greatest efficacy. In SCC47 cells (HPV+ human HNSCC), all drugs reduced cell number relative to control (Cisplatin 50-500 µM p<0.0007 compared to control, A-platin 1-500 µM p<0.02 compared to control, G-platin 10-500 µM p<0.008 compared to control). A-platin was again the most efficacious. In Primary human tonsil epithelial cells (HTE), all drugs reduced cell number (cisplatin 10-500 µM p<0.04 compared to control, A-platin 1-500 µM p<0.012 compared to control, G-platin 1-500 µM p<0.007 compared to control). A-platin was again the most potent but showed less of an effect in the primary cells compared to the cancer cells—especially at higher doses.

Figure 8:
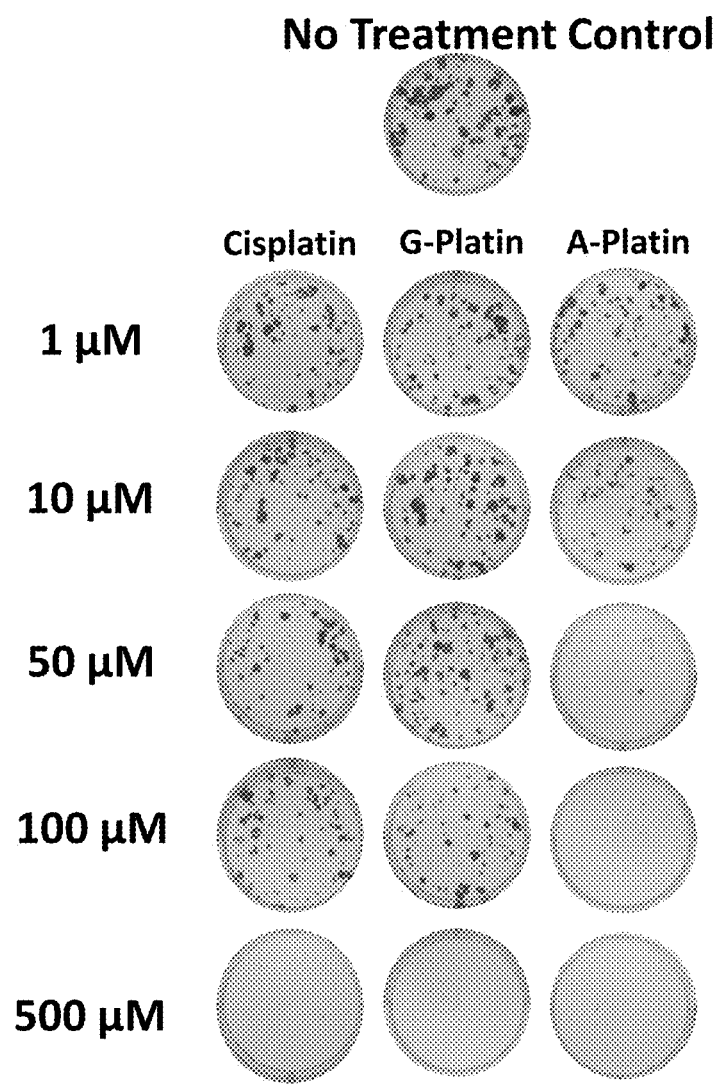
FIG. 8 shows images from cell growth assays, according to certain embodiments.
Figure 9:
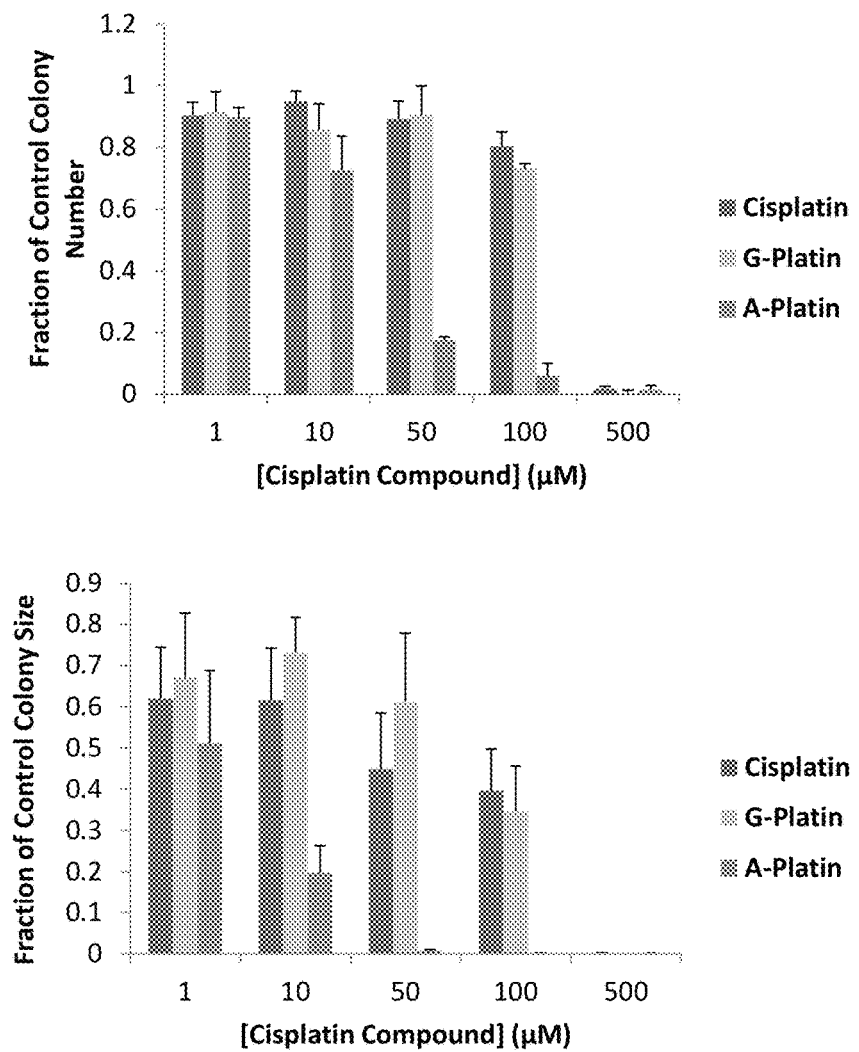
FIG. 9 shows data colony formation assays, according to certain embodiments.

Additional assays were performed in Mouse Tonsil Epithelial E6/E7/Ras/Luciferase (MEERL) cells. Briefly, MEERL cells were plated per well (6-well plate) in triplicate, treatments began the next day for 12 hours, colonies fixed (70% EtOH) and stained (0.5% crystal violet in 10% EtOH) on day 6 from plating. Results are best seen in FIG. 8 and show A-platin to have the greatest efficacy in inhibiting cell colony growth.

Figure 10:
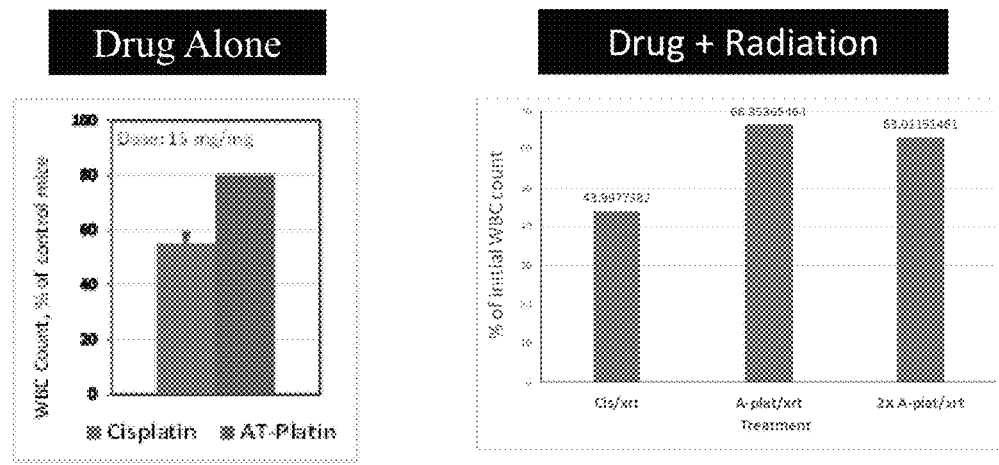
FIG. 10 shows data from white blood cell count assays, according to certain embodiments.
Figure 11:
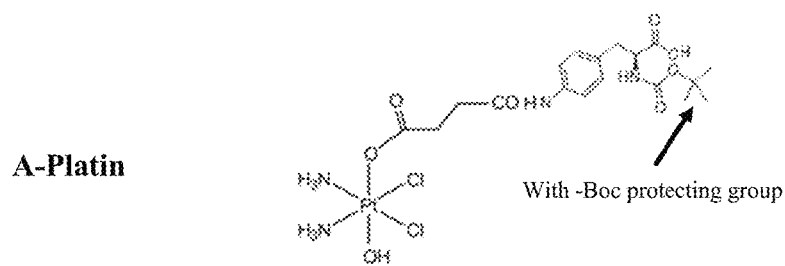
FIG. 11 shows the structures A-platin and G-platin, according to certain embodiments.
Figure 11:
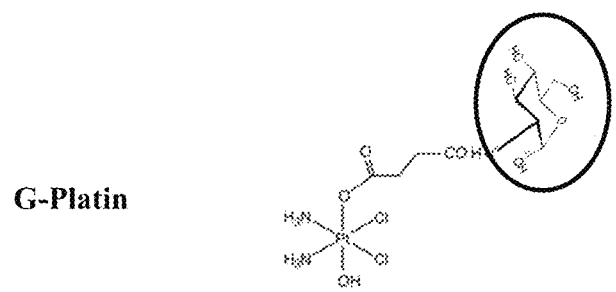
Figure 12:
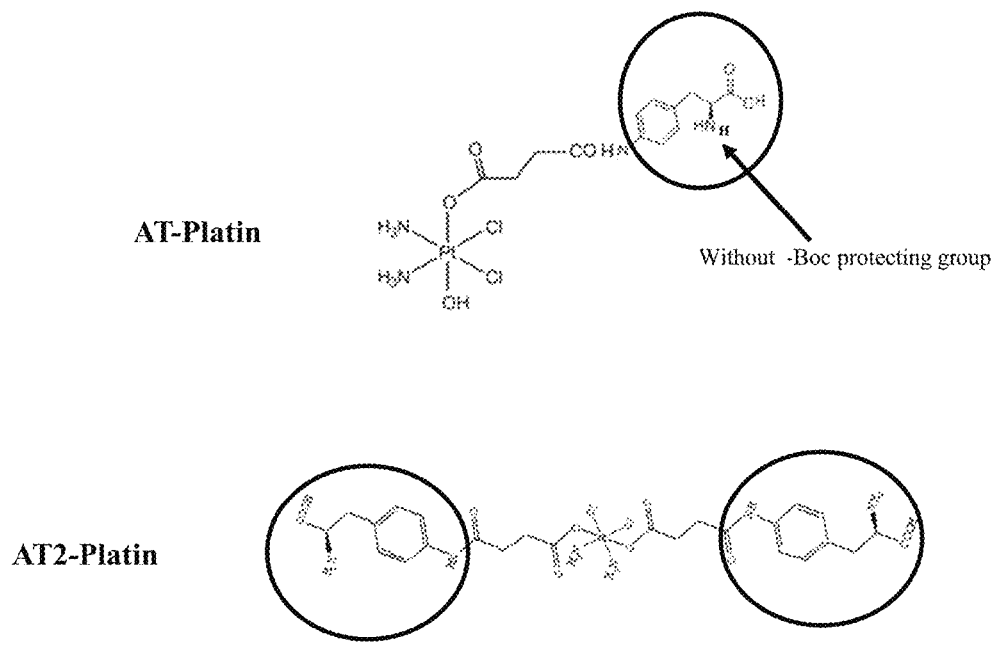
FIG. 12 shows the structures of AT-platin and AT2-platin, according to certain embodiments.

White blood cell (WBC) counts are important for immune mediated tumor clearance. In order to assess the level of WBC toxicity of induced by A-Platin relative the WBC lose was quantified in mice following treatment with drug along and drug administered in conjunction with radiation. As best shown in FIG. 10, AT-Platin induced less white blood cell loss in both drug treatment alone groups and drug+radiation groups.

Although the present invention has been described with reference to preferred embodiments, persons skilled in the art will recognize that changes may be made in form and detail without departing from the spirit and scope of the invention.

What is claimed is:

1. An anticancer composition comprising an antineoplastic platin compound and a conjugated targeting moiety with or without a chemical linker, wherein the targeting moiety is a L-type amino acid.

2. The composition of claim 1, wherein the platin is cisplatin.

3. The composition of claim 1, wherein the amino acid is selected from a group comprising: leucine, isoleucine, histidine, methionine, phenylalanine, tyrosine, valine, and tryptophan.

4. The composition of claim 3, wherein the amino acid is phenylalanine.

5. The composition of claim 1, wherein the conjugated targeting moiety binds L-type amino acid transporter (LAT) or ASCT.

6. The composition of claim 1, wherein the composition has greater cancer cell killing efficacy than the antineoplastic compound without the conjugated targeting moiety.

7. The composition of claim 1, wherein the composition has greater potency than the antineoplastic compound without the conjugated targeting moiety.

8. The composition of claim 1, wherein administration of the composition induces less toxicity than administration of the antineoplastic compound without the conjugated targeting moiety.

9. The composition of claim 8, wherein administration of the composition induces less nephrotoxicity or immune toxicity than administration of the antineoplastic compound without the conjugated targeting moiety.

10. An anticancer composition, having the structure:

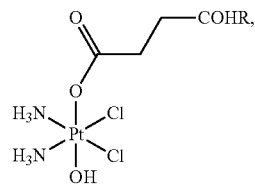

wherein R is a L-type amino acid.

11. The composition of claim 10, wherein the amino acid is phenylalanine.

12. A method for treating cancer in a subject in need thereof, the method comprising administering to the subject an effective amount of the composition of claim 10 and a pharmaceutically acceptable carrier thereof.

13. The method of claim 12, wherein administration of the composition induces tumor cell clearance.

14. The method of claim 12, further comprising administering the composition intravenously, intraperitoneally, intramuscularly, orally, subcutaneously, intraocularly, intratumor injection or transdermally or delivered directly to tumor organ by invasive techniques.

15. The method of claim 12, further comprising administering the composition in conjunction with at least one other treatment or therapy, wherein the other treatment or therapy comprises co-administering another anti-neoplastic agent.

16. The method of claim 12, wherein the compound is administered alone or in combination with other chemical based therapeutics, radiation therapy, thermal therapy, physical therapy, phototherapy, or dietary therapy.

* * * * *